United States Patent [19]

Yamato et al.

[11] 4,390,548
[45] Jun. 28, 1983

[54] TRANS-Δ²-PGE ALKYLSULPHONYL AMIDES

[75] Inventors: Takashi Yamato, Takatsuki; Hirofumi Endo, Fujinomiya; Kimiichiro Matsumoto; Hajimu Miyake, both of Takatsuki, all of Japan

[73] Assignee: Ono Pharmaceutical Co., Ltd., Osaka, Japan

[21] Appl. No.: 257,102

[22] Filed: Apr. 24, 1981

[30] Foreign Application Priority Data

Apr. 28, 1980 [JP] Japan ................... 55-55337

[51] Int. Cl.³ ............... C07C 143/75; A61K 31/18
[52] U.S. Cl. ........................ 424/321; 564/98; 564/99; 556/419; 549/28; 542/426
[58] Field of Search ............... 260/345.7 P, 345.8 P, 260/347.2; 564/98, 99; 542/426; 556/419; 549/28, 414, 416; 424/321

[56] References Cited

U.S. PATENT DOCUMENTS

| | | | |
|---|---|---|---|
| 3,931,296 | 1/1976 | Hayashi et al. | 260/345.7 P |
| 3,954,741 | 5/1976 | Schaaf et al. | 560/106 |
| 4,024,174 | 5/1977 | Hayashi et al. | 260/345.7 P |
| 4,024,179 | 3/1977 | Bindra et al. | 260/345.7 P |
| 4,034,003 | 7/1977 | Hayashi et al. | 260/345.7 P |
| 4,073,934 | 2/1978 | Skuballa et al. | 260/345.7 P |
| 4,191,694 | 3/1980 | Skuballa et al. | 260/345.7 P |

*Primary Examiner*—Nicky Chan
*Attorney, Agent, or Firm*—Stevens, Davis, Miller & Mosher

[57] ABSTRACT

Prostaglandin analogues of the formula:

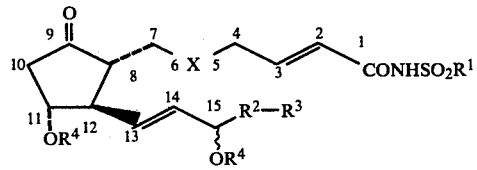

(wherein $R^1$ represents an alkyl group containing from 1 to 4 carbon atoms, $R^2$ represents a single bond or an alkylene group containing from 1 to 5 carbon atoms, $R^3$ represents a hydrogen atom, an alkyl or alkoxy group containing from 1 to 8 carbon atoms, a cycloalkyl or cycloalkyloxy group containing from 4 to 7 carbon atoms and being unsubstituted or substituted by at least one alkyl group containing from 1 to 8 carbon atoms, or a phenyl or phenoxy group unsubstituted or substituted by at least one halogen atom, trifluoromethyl group or alkyl group containing from 1 to 4 carbon atoms, $R^4$ represents a hydrogen atom or a hydroxy-protecting group which may be removed under acidic conditions, X represents an ethylene group or a cis-vinylene group, the double bonds between the carbon atoms in positions 2 and 3 and between the carbon atoms in positions 13 and 14 are both in trans-configuration, and the wavy line attached to the carbon atom in position 15 represents α- or β-configuration or a mixture thereof, provided that, when $R^2$ represents a single bond, $R^3$ does not represent an alkoxy group, a cycloalkoxy group or a phenoxy group) and cyclodextrin clathrates thereof are useful compounds: those in which $R^4$ represents a hydrogen atom possess selective prostaglandin-like properties.

11 Claims, No Drawings

TRANS-Δ²-PGE ALKYLSULPHONYL AMIDES

DESCRIPTION

This invention is concerned with new prostaglandin analogues.

Prostaglandins are derivatives of prostanoic acid which has the following formula:

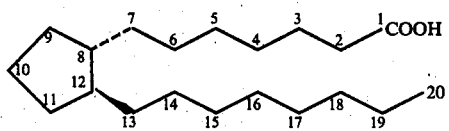

Various types of prostaglandins are known, the types depending inter alia on the structure and substituents on the alicyclic ring. For example, the alicyclic ring of prostaglandin E(PGE) has the structure:

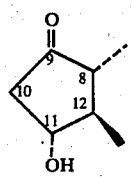

The dotted lines in the foregoing formulae and in other formulae throughout this specification denote, in accordance with generally accepted rules of nomenclature, that the attached grouping lies behind the general plane of the ring system, i.e. that the grouping is in α-configuration, the thickened lines denote that the grouping lies in front of the general plane of the system, i.e. that the grouping is in β-configuration, and the wavy line ∼ indicates that the grouping is in α- or β-configuration.

Such compounds are sub-classified according to the position of double bond(s) in the side chain(s) attached to the 8- and 12-positions of the alicyclic ring. Thus PG$_1$ compounds have a trans-double bond between C$_{13}$–C$_{14}$(trans-Δ$^{13}$) and PG$_2$ compounds have a cis-double bond between C$_5$–C$_6$ and a trans-double bond between C$_{13}$–C$_{14}$(cis-Δ$^5$, trans-Δ$^{13}$). For example, prostaglandin E$_1$ (PGE$_1$) is characterised by the following structure III.

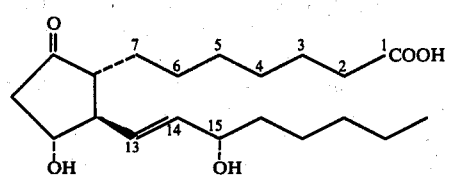

The structure of PGE$_2$, as a member of the PG$_2$ group, corresponds to that of formula III with a cis-double bond between the carbon atoms in positions 5 and 6.

Moreover, when one or more methylene groups are eliminated from the aliphatic group attached to the 12-position of the alicyclic ring of the prostaglandins the compounds are known, in accordance with the usual rules of organic nomenclature, as nor-prostaglandins and, when more than one methylene group is eliminated, the number is indicated by di-, tri- etc. before the prefix "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGE's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. PGE$_1$ inhibits blood platelet aggregation and also removes the thrombus and prevents thrombosis. PGE's have a stimulating effect on smooth muscle and increase the intestinal peristalsis; these actions indicate therapeutic utility on post-operative ileus and as purgatives. PGE's may also be used as oxytocics, as abortifacients in the first and second trimesters; in the post-labour abortion of the placenta, and as oral contraceptives because they regulate the sexual cycle of female mammals. PGE's have vasodilator and diuretic activities. They are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree, or hitherto unknown pharmacological properties. It has now been found, after research and experimentation, that by replacing the carboxy group attached to the 1-position of prostaglandin E and certain analogues thereof by an amide group substituted by a sulphonyl group (i.e. —CONHSO$_2$R$^1$, R$^1$ being as hereinafter defined) and by introducing a trans (i.e. E) double bond between the carbon atoms in positions 2 and 3, new prostaglandin E analogues are obtained which possess the pharmacological properties of the 'natural' prostaglandins and are, in some aspects of their activities, an improvement, for example possessing an enhanced strength of activity and/or greater selectivity.

The present invention accordingly provides the new prostaglandin E analogues of the general formula:

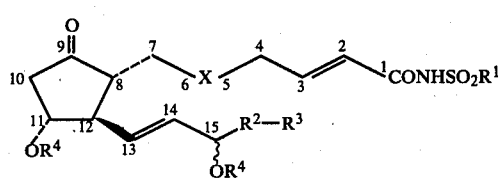

[wherein R$^1$ represents an alkyl group containing from 1 to 4 carbon atoms, R$^2$ represents a single bond or an alkylene group containing from 1 to 5 carbon atoms, R$^3$ represents a hydrogen atom, an alkyl or alkoxy group containing from 1 to 8 carbon atoms, a cycloalkyl or cycloalkyloxy group containing from 4 to 7 carbon atoms and being unsubstituted or substituted by at least one alkyl group containing from 1 to 8 carbon atoms, or a phenyl or phenoxy group unsubstituted or substituted by at least one halogen atom, trifluoromethyl group or alkyl group containing from 1 to 4 carbon atoms, $R^4$ represents a hydrogen atom or a hydroxy-protecting group which may be removed under acidic conditions, X represents an ethylene group (—CH$_2$CH$_2$—) or a cis-vinylene group

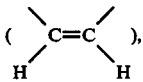

the double bonds between the carbon atoms in positions 2 and 3 and between the carbon atoms in positions 13 and 14 are both in trans- (i.e. E) configuration, and the wavy line ⁓ attached to the carbon atom in position 15 represents α- or β-configuration (i.e. S— or R—configuration) or a mixture thereof, provided that, when $R^2$ represents a single bond, $R^3$ does not represent an alkoxy group, a cycloalkoxy group or a phenoxy group] and, when $R^4$ represents a hydrogen atom, cyclodextrin clathrates thereof. When the symbols $R^4$ in formula IV represent hydroxy-protecting groups which may be removed under acidic conditions those groups may be the same or different.

The present invention is concerned with all compounds of general formula IV in the optically active "natural" form or its enantiomeric form, or mixtures thereof (particularly the racemic form consisting of equimolecular mixtures of "natural" form and its enantiomeric form).

As will be apparent to those skilled in the art, the compounds of general formula IV have at least four centres of chirality, these four centres of chirality being at the C-8, C-11, C-12 and C-15 carbon atoms. Further centres of chirality may occur when the alkyl and alkylene groups represented by $R^1$, $R^2$ or $R^3$ are branched-chain. The presence of chirality leads, as is well known, to the existence of isomerism. However, the compounds of general formula IV all have such a configuration that the side-chains attached to the alicyclic ring carbon atoms in the positions identified as 8 and 12 are trans with respect to each other. Accordingly, all isomers of general formula IV and mixtures thereof which have those substituent groups attached to the ring carbon atoms in positions 8 and 12 in the trans-configuration and have a hydroxy group as depicted in the 15-position are to be considered within the scope of general formula IV.

In this specification, it is to be understood that alkyl and alkylene groups and alkyl and alkylene moieties may be straight- or branched-chain. It is also to be understood that double bonds depicted between the carbon atoms in positions 2 and 3 and positions 13 and 14 are all trans.

Examples of the alkyl groups represented by $R^1$ are methyl, ethyl, propyl, isopropyl, butyl, isobutyl, sec-butyl and tert-butyl; $R^1$ preferably represents a methyl group.

Examples of the group —$R^2$-$R^3$ are methyl, ethyl, 1-methylethyl, propyl, 1-methylpropyl, 2-methylpropyl, 1-ethylpropyl, butyl, 1-methylbutyl, 2-methylbutyl, 3-methylbutyl, 1-ethylbutyl, 2-ethylbutyl, pentyl, 1-methylpentyl, 2-methylpentyl, 3-methylpentyl, 4-methylpentyl, 1,1-dimethylpentyl, 1,2-dimethylpentyl, 1,4-dimethylpentyl, 1-ethylpentyl, 2-ethylpentyl, 1-propylpentyl, 2-propylpentyl, hexyl, 1-methylhexyl, 2-methylhexyl, 1,1-dimethylhexyl, 1-ethylhexyl, 2-ethylhexyl, heptyl, 2-ethylheptyl, nonyl, undecyl, cyclobutyl, 1-propylcyclobutyl, 1-butylcyclobutyl, 1-pentylcyclobutyl, 1-hexylcyclobutyl, 2-methylcyclobutyl, 2-propylcyclobutyl, 3-ethylcyclobutyl, 3-propylcyclobutyl, 2,3,4-triethylcyclobutyl, cyclopentyl, cyclopentylmethyl, 1-cyclopentylethyl, 2-cyclopentylethyl, 2-cyclopentylpropyl, 3-cyclopentylpropyl, 2-pentylcyclopentyl, 2,2-dimethylcyclopentyl, 3-ethylcyclopentyl, 3-propylcyclopentyl, 3-butylcyclopentyl, 3-tert-butylcyclopentyl, (1-methyl-3-propyl)cyclopentyl, (2-methyl-3-propyl)cyclopentyl, (2-methyl-4-propyl)cyclopentyl, cyclohexyl, cyclohexylmethyl, 1-cyclohexylethyl, 2-cyclohexylethyl, 3-cyclohexylpropyl, (1-methyl-2-cyclohexyl)ethyl, 2-cyclohexylpropyl, (1-methyl-1-cyclohexyl)ethyl, 4-cyclohexylbutyl, 3-ethylcyclohexyl, 3-isopropylcyclohexyl, 4-methylcyclohexyl, 4-ethylcyclohexyl, 4-propylcyclohexyl, 4-tert-butylcyclohexyl, 2,6-dimethylcyclohexyl, 2,2-dimethylcyclohexyl, (2,6-dimethyl-4-propyl)cyclohexyl, 1-methylcyclohexylmethyl, cycloheptyl, cycloheptylmethyl, 1-cycloheptylethyl, 2-cycloheptylethyl, phenyl, benzyl, 1-phenylethyl, 2-phenylethyl, 3-phenylpropyl, 4-phenylbutyl, 5-phenylpentyl, (1-methyl-2-phenyl)ethyl, (1,1-dimethyl-2-phenyl)ethyl, (1-methyl-1-phenyl)ethyl, 1-phenylpentyl, phenoxymethyl, 2-phenoxyethyl, 3-phenoxypropyl, 4-phenoxybutyl, 5-phenoxypentyl, 3-chlorophenoxymethyl, 4-chlorophenoxymethyl, 4-fluorophenoxymethyl, 3-trifluoromethylphenoxymethyl, 2-methylphenoxymethyl, 3-methylphenoxymethyl, 4-methylphenoxymethyl, 4-ethylphenoxymethyl, 4-tert-butylphenoxymethyl, 4-sec-butylphenoxymethyl, propoxymethyl, isopropoxymethyl, butoxymethyl, pentyloxymethyl, hexyloxymethyl, 1-ethoxyethyl, 1-propoxyethyl, 1-isopropoxyethyl, 1-neopentyloxyethyl, 1-pentyloxyethyl, (1-methyl-1-ethoxy)ethyl, (1-methyl-1-propoxy)ethyl, (1-methyl-1-isobutoxy)ethyl, (1-methyl-1-neopentyloxy)ethyl, (1-methyl-1-butoxy)ethyl, (1-methyl-1-isopentyloxy)ethyl, (1-methyl-1-pentyloxy)ethyl, 2-ethoxyethyl, 2-propoxyethyl, 2-butoxyethyl, 2-(1-ethylbutoxy)ethyl, 2-pentyloxyethyl, 1-ethoxypropyl, 1-propoxypropyl, 1-(2-methylbutoxy)propyl, 1-pentyloxypropyl, 2-methoxypropyl, 3-methoxypropyl, 3-ethoxypropyl, 3-propoxypropyl, 3-sec-butoxypropyl, 3-isobutoxypropyl, 3-butoxypropyl, (1-methyl-2-methoxy)ethyl, (1-methyl-2-ethoxy)ethyl, (1-methyl-2-isobutoxy)ethyl, 1-pentyloxybutyl, (1-pentyloxy-2-methyl)propyl, 4-methoxybutyl, 4-ethoxybutyl, 4-propoxybutyl, (1-methyl-3-methoxy)propyl, (1-methyl-3-propoxy)propyl, (2-methyl-3-methoxy)propyl, (1,1-dimethyl-2-ethoxy)ethyl, (1,1-dimethyl-2-propoxy)ethyl, (1,1-dimethyl-2-isobutoxy)ethyl, 5-methoxypentyl, 5-ethoxypentyl, 1-pentyloxypentyl, (1-ethyl-3-propoxy)propyl, cyclobutyloxymethyl, cyclopentyloxymethyl, cyclohexyloxymethyl, cycloheptyloxymethyl, 2-cyclopentyloxyethyl and 2-cyclohexyloxyethyl.

Preferably the grouping —$R^2$-$R^3$ represents n-pentyl or n-hexyl unsubstituted or substituted by one or two methyl group(s), or $R^2$ represents a single bond or a methylene or ethylene group and $R^2$ represents a cyclopentyl or cyclohexyl group unsubstituted or substituted by an alkyl group containing from 1 to 4 carbon atoms, or a phenyl or phenoxy group unsubstituted or substituted by at least one halogen atom or trifluoromethyl group; particularly preferred examples of the grouping —$R^2$-$R^3$ are n-pentyl, 1-methylpentyl, 2-methylpentyl, 1,1-dimethylpentyl, hexyl, 2-methylhexyl, cyclopentyl, cyclopentylmethyl, 2-cyclopentylethyl, 3-ethylcyclopentyl, 3-propylcyclopentyl, 3-butylcyclopentyl, cyclohexyl, cyclohexylmethyl, 2-cyclohexylethyl, 4-methylcyclohexyl, 4-propylcyclohexyl, benzyl, 2-phenylethyl, phenoxymethyl, 3-chlorophenoxymethyl, 4-cyclophenoxymethyl, and 3-trifluoromethylphenoxymethyl. 4-Chlorophenoxymethyl and 1,1-dimethylpentyl are most preferred.

The hydroxy-protecting groups represented by $R^4$ which may be removed under acidic conditions are groups which have no influence on other parts of the compounds during elimination of the protecting groups and which are easily removed under mild acidic conditions, for example:

(1) a heterocyclic group such as a tetrahydropyran-2-yl, tetrahydrofuran-2-yl or tetrahydrothiopyran-2-yl group;

(2) an ether group such as a 1-ethoxyethyl, 1-methoxy-1-methylethyl, 1-methoxycyclohexyl or 1-methoxy-1-phenylethyl group; and (3) a tri-substituted silyl group such as a trimethylsilyl, triethylsilyl, tributylsilyl, tert-butyldimethylsilyl, tribenzylsilyl or triphenylsilyl group.

Preferably $R^4$ represents a hydrogen atom or a tetrahydropyran-2-yl group.

The wavy line attached to the carbon atom in position 15 is preferably in α-configuration.

According to a feature of the present invention, prostaglandin analogues of general formula IV wherein $R^4$ represents a hydrogen atom and the other symbols are as hereinbefore defined, i.e. compounds of the general formula:

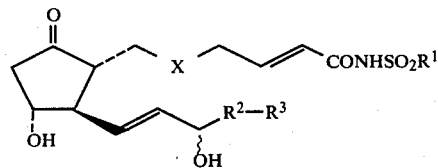

IVA (wherein the various symbols are as hereinbefore defined) are prepared by the conversion to hydroxy groups of the groups $OR^5$ of compounds of general formula IV wherein $R^4$ is other than a hydrogen atom and the other symbols are as hereinbefore defined, i.e. compounds of the general formula:

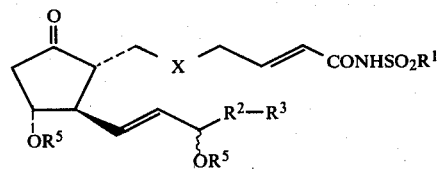

IVB (wherein $R^5$ represents a hydroxy-protecting group which may be removed under acidic conditions and the other symbols are as hereinbefore defined) under acidic conditions. The hydroxy-protecting groups represented by $R^5$ may be the same or different.

The groups $OR^5$ may be converted to hydroxy groups by known methods: the conversion is generally carried out under mild acidic conditions. (By the expression "known methods" as used in this specification is meant methods heretofore used or described in the chemical literature). For example, the reaction can be conducted:

(1) at a temperature from ambient to 75° C. in an aqueous solution of an organic acid such as acetic acid, propionic acid, oxalic acid or p-toluenesulphonic acid, or in an aqueous solution of an inorganic acid such as hydrochloric acid, sulphuric acid or phosphoric acid, preferably in the presence of a water-miscible organic solvent such as an alkanol containing from 1 to 4 carbon atoms (e.g. methanol or ethanol, preferably methanol) or an ether (e.g. 1,2-dimethoxyethane, dioxan or tetrahydrofuran, preferably tetrahydrofuran);

(2) at a temperature from 0° C. to 45° C. in an absolute alkanol containing from 1 to 4 carbon atoms (e.g. absolute methanol or absolute ethanol) in the presence of an organic acid such as p-toluenesulphonic acid or trifluoroacetic acid; or (3) at a temperature from 10° C. to 60° C. in an absolute alkanol containing from 1 to 4 carbon atoms (e.g. absolute methanol or absolute ethanol) in the presence of p-toluenesulphonic acid-pyridine complex or trifluoroacetic acid-pyridine complex.

Preferably, the conversion of the groups $OR^5$ to hydroxy groups is carried out using a mixture of dilute hydrochloric acid and tetrahydrofuran, a mixture of dilute hydrochloric acid and methanol, a mixture of acetic acid, water and tetrahydrofuran, a mixture of phosphoric acid, water and tetrahydrofuran, a mixture of p-toluenesulfonic acid and methanol, a mixture of p-toluenesulphonic acid-pyridine complex and methanol, or a mixture of trifluoroacetic acid-pyridine complex and methanol.

Compounds of general formula IVB wherein the various symbols are as hereinbefore defined can be obtained by oxidising to an oxo group the hydroxy group attached to the C-9 carbon atom of compounds of the general formula:

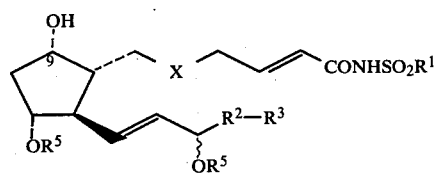

V wherein the various symbols are as hereinbefore defined.

The oxidation of the hydroxy group to an oxo group may be carried out by known methods, for example as described in:

(a) "Synthetic Organic Chemistry III, Organic Synthesis 1", pp. 176–206 (compiled by Tetsuji Kameya and published by Nankodo (Japan) on Aug. 1, 1976) or (b) "Compendium of Organic Synthetic Methods" vol. 1, vol. 2 and vol. 3, section 48 or 168 (published by John Wiley & Sons, Inc. (U.S.A.) in 1971, 1974 and 1977, respectively). The oxidation is preferably carried out under mild neutral conditions using, for example, dimethylsulphide-N-chlorosuccinimide complex, thioanisole-N-chlorosuccinimide complex, dimethylsulphide-chlorine complex, thioanisole-chlorine complex [see J. Amer. Chem. Soc., 94, 7586 (1972) with respect to these complexes], dicyclohexylcarbodiimide-dimethylsulphoxide complex [see J. Amer. Chem. Soc., 87, 5661 (1965)], pyridinium chlorochromate ($C_5H_5NHCrO_3Cl$) [see Tetrahedron Letters, 2647 (1975)], sulphuric anhydride-pyridine complex [see J. Amer. Chem. Soc., 89, 5505 (1967)], chromyl chloride [see J. Amer. Chem. Soc., 97, 5929 (1975)], chromium trioxide-pyridine complex (for example, Collins' reagent), Jones' reagent or chromic acid solution (prepared from chromium trioxide, manganese sulphate, sulphuric acid, and water).

Oxidation using a dimethylsulphide-N-chlorosuccinimide complex, a thioanisole-N-chlorosuccinimide complex, a dimethylsulphide-chlorine complex or a thioanisole-chlorine complex is carried out by reaction in a halogenated hydrocarbon such as chloroform, methylene chloride or carbon tetrachloride, or in toluene, at a temperature from −30° C. to 0° C., followed by treatment with triethylamine.

Oxidation using a dicyclohexylcarbodiimidedimethylsulphoxide complex is usually carried out in excess dimethylsulphoxide at room temperature in the presence of an acid catalyst such as phosphoric acid, phosphorous acid, cyanoacetic acid, pyridine-phosphoric acid salt, or trifluoroacetic acid.

Oxidation using pyridinium chlorochromate is carried out in a halogenated hydrocarbon such as chloroform, methylene chloride, or carbon tetrachloride usually at room temperature in the presence or absence of sodium acetate.

Oxidation using a sulphuric anhydride-pyridine complex is usually carried out in dimethylsulphoxide at room temperature in the presence of triethylene.

Oxidation using chromyl chloride is usually carried out in a halogenated hydrocarbon such as chloroform, methylene chloride, or carbon tetrachloride in the presence of tert-butanol and pyridine at a temperature from −30° C. to the reflux temperature of the reaction mixture.

Oxidation using a chromium trioxide-pyridine complex is carried out in a halogenated hydrocarbon such as chloroform, methylene chloride, or carbon tetrachloride at a temperature from ambient to 0° C., preferably at 0° C.

Oxidation using Jones' reagent is usually carried out at a temperature not higher than ambient.

Oxidation using a chromic acid solution is generally carried out in diethyl ether at a temperature from −10° C. to 5° C.

Compounds of general formula V wherein the various symbols are as hereinbefore defined can be obtained by oxidatively eliminating the group —$R^6$—$R^7$ of compounds of the general formula:

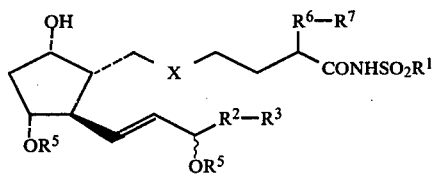
VI

[wherein $R^6$ represents a sulphur atom and $R^7$ represents an alkyl group containing from 1 to 4 carbon atoms or a phenyl group of the general formula:

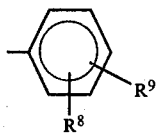
VIA (wherein $R^8$ and $R^9$, which may be the same or different and may occupy any of the free positions on the phenyl ring, each represents a hydrogen atom, a chlorine atom, a trifluoromethyl group, a methoxy group or a nitro group), or $R^6$ represents a selenium atom and $R^7$ represents a phenyl group of formula VIA (wherein $R^8$ and $R^9$ are as hereinbefore defined) and the other symbols are as hereinbefore defined].

Compounds of general formula VI wherein $R^6$ represents a selenium atom can be converted to compounds of general formula V by: (1) reaction with hydrogen peroxide in a mixture of ethyl acetate and tetrahydrofuran or a mixture of ethyl acetate and methanol, preferably in the presence of calcium carbonate or an alkali metal bicarbonate (e.g. sodium bicarbonate or potassium bicarbonate) at a temperature not higher than 45° C., preferably from 25° C. to 35° C., or (2) reaction with sodium periodate in an aqueous solution of an alkanol containing from 1 to 4 carbon atoms, such as aqueous methanol or aqueous ethanol, preferably in the presence of an alkali metal bicarbonate such as sodium bicarbonate or potassium bicarbonate at a temperature not higher than 45° C., preferably 0° C.

Compounds of general formula VI wherein $R^6$ represents a sulphur atom can be converted to compounds of the general formula:

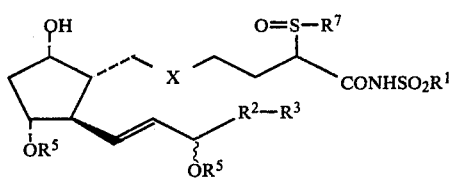
VII (wherein the various symbols are as hereinbefore defined) by reaction with m-chloroperbenzoic acid in an inert organic solvent, such as diethyl ether or methylene chloride, at a temperature from ambient to −78° C., preferably not higher than 0° C., or by oxidation under the conditions described above for the conversion of compounds of general formula VI, wherein $R^6$ represents a selenium atom, to compounds of general formula V.

Compounds of general formula VII wherein $R^7$ represents an alkyl group or a phenyl group of general formula VIA, wherein $R^8$ and $R^9$ are as hereinbefore defined, can be converted to compounds of general formula V by reaction in toluene preferably in the presence of calcium carbonate or trimethyl phosphite at a temperature not higher than the reflux temperature of the reaction mixture, and compounds of general formula VII wherein $R^7$ represents a phenyl group of general formula VIA, wherein $R^8$ and $R^9$ are as hereinbefore defined, can be converted to compounds of general formula V by reaction in carbon tetrachloride preferably in the presence of calcium carbonate or trimethyl phosphate at a temperature not higher than the reflux temperature of the reaction mixture.

Compounds of general formula VI wherein the various symbols are as hereinbefore defined can be obtained by reaction of a reactive derivative of an acid of the general formula:

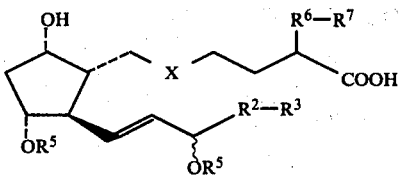
VIII (wherein the various symbols are as hereinbefore defined) with a compound of the general formula:

   IX (wherein M represents an alkali metal, such as sodium, potassium or lithium, and $R^1$ is as hereinbefore defined) in an inert organic solvent such as methylene chloride, methanol, diethyl ether, tetrahydrofuran, 1,2-dimethoxyethane, benzene, toluene, dioxan, acetonitrile, N,N-dimethylformamide, hexamethylphosphoramide (hereinafter abbreviated to HMPA), or a mixture of two or more of them at room temperature or, if necessary, with heating or cooling.

Examples of suitable reactive derivatives of the acid of general formula VIII are acid halides (e.g. acid chlorides or acid bromides), acid anhydrides, mixed acid anhydrides with alkyl carbonates or inorganic halides (e.g. phosphorus oxychloride or thionyl chloride), active esters such as p-nitrophenyl esters, and active esters with dicyclohexylcarbodiimide. Preferably, the reactive derivative of the acid of general formula VIII is prepared in situ, for example in N,N-dimethylformamide using triethylamine and isobutyl chloroformate at 0° C., and is then reacted with the sodium derivative of general formula IX in the presence of HMPA at a temperature from ambient to 0° C.

Compounds of general formula IX are known compounds and can be prepared by known methods.

Acids of general formula VIII may be obtained by saponification of alkyl esters of the acids, i.e. compounds of the general formula:

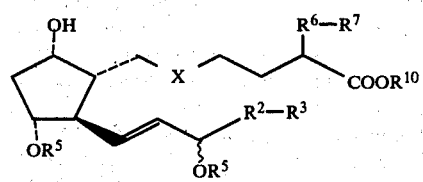
X (wherein $R^{10}$ represents an alkyl group containing from 1 to 4 carbon atoms, and the other symbols are as hereinbefore defined) by known methods, for example, in methanol using an aqueous solution of potassium hydroxide.

Compounds of general formula VIII or X may be obtained by the process which comprises reacting compounds of the general formula:

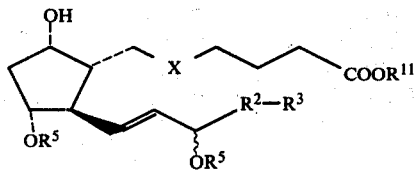
XI (wherein $R^{11}$ represents a hydrogen atom or an alkyl group containing from 1 to 4 carbon atoms, and the other symbols are as hereinbefore defined) with compounds of the general formula:

   XII (wherein $R^{12}$ and $R^{13}$ may be the same or different and each represents an alkyl group containing from 1 to 6 carbon atoms or a cycloalkyl group containing from 3 to 6 carbon atoms) such as lithium diisopropylamide, to obtain compounds of the general formula:

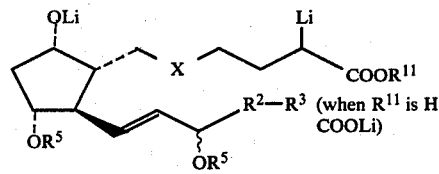
XIII (wherein the various symbols are as hereinbefore defined), reacting the resulting compounds of general formula XIII with a selenium compound of the general formula:

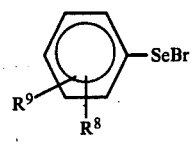
XIV (wherein $R^8$ and $R^9$ are as hereinbefore defined) or a compound of the general formula:

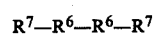   XV (wherein the symbols $R^6$ both represent sulphur atoms and the symbols $R^7$ are identical and each represents an alkyl group containing from 1 to 4 carbon atoms or a phenyl group of general formula VIA, wherein $R^8$ and $R^9$ are as hereinbefore defined, or the symbols $R^6$ both represent selenium atoms and the symbols $R^7$ are identical and each represents a phenyl group of general formula VIA, wherein $R^8$ and $R^9$ are as hereinbefore defined) and hydrolysing the resulting compounds, for example, using an aqueous solution of ammonium chloride.

The reaction between the compounds of general formula XI and the lithiated amines of general formula XII may be carried out in an inert organic solvent (e.g. tetrahydrofuran, HMPA, diethyl ether, hexane, pentane, or a mixture of two or more of them), (1) when $R^{11}$ represents an alkyl group, at a low temperature of, for example, from 0° C. to −78° C., preferably −78° C., or (2) when $R^{11}$ represents a hydrogen atom, at a low temperature of, for example, from room temperature to 0° C., preferably 0° C., in the presence of HMPA.

The reaction between the compounds of general formula XIII and the compounds of general formula XIV or XV may be carried out in an inert organic solvent (e.g. tetrahydrofuran, HMPA, diethyl ether, hexane, pentane, or a mixture of two or more of them) at a low temperature, for example, from room temperature to −78° C. when $R^{11}$ represents an alkyl group or from room temperature to 0° C. when $R^{11}$ represents a hydrogen atom.

Preferred examples of the group of formula VIA (wherein $R^8$ and $R^9$ are as hereinbefore defined) are phenyl, 2-nitrophenyl, 4-nitrophenyl, 4-chlorophenyl, 2-trifluoromethylphenyl, 3-trifluoromethylphenyl, 2-trifluoromethyl-4-nitrophenyl, and 4-methoxyphenyl.

Starting materials of general formula XI can be obtained by the methods described in the following literature references and patent specifications, or obvious modifications thereof:

(1) when the group $-R^2-R^3$ represents a pentyl group, as described in J. Amer. Chem. Soc., 91, 5675 (1969) or ibid., 92, 397 (1970);

(2) when the group $-R^2-R^3$ represents an alkyl group, as described in Japanese Patent Kokai Nos. 42675/72, 54068/73, 64073/73, 124048/74, 95250/75, 96543/75 and 101340/75, British Patent Specification Nos. 1398291, 1483240 and 1540427, U.S. Pat. No. 4,024,174, and Belgian Pat. No. 850084;

(3) when $R^3$ of the group $-R^2-R^3$ represents a cycloalkyl group, as described in Japanese Patent Kokai Nos. 109353/74, 95250/75, 96543/75, 123647/75, 148339/75, 122040/76, 125256/76, 27753/77 and 25544/78, British Patent Specification Nos. 1464916, 1488141, 1483240, 1484210 and 1545213, U.S. Pat. Nos. 3,966,792, 4,034,003, 4,024,174, 4,045,468 and 4,087,620, and Belgian Pat. No. 844256;

(4) when $R^3$ of the group $-R^2-R^3$ represents a phenyl group or a phenoxy group, as described in Japanese Patent Kokai Nos. 95250/75, 96543/75, 59841/76, 101961/76 and 25745/77, British Patent Specifications Nos. 1483240 and 1521747, U.S. Pat. Nos. 4,024,174 and 4,065,632, and Belgian Pat. No. 845348;

(5) when $R^3$ of the group $-R^2-R^3$ represents an alkoxy group or a cycloalkyloxy group, as described in Japanese Patent Kokai Nos. 54349/74, 100060/74, 137959/75, 36442/76, 7939/77 and 31054/77, British Patent Specifications Nos. 1440601-3[(1)], 1456511[(2)], 1511261[(3)] and 1515896[(4)], U.S. Pat. Nos. 4,094,899[(1)] and 4,061,671[(3)], and Belgian Pat. Nos. 800350[(1)], 807047[(2)], 827529[(3)], 831649[(4)] and 843420[(5)].

(1)—Derwent No. 78456U
(2)—Derwent No. 38270V
(3)—Derwent No. 70671W
(4)—Derwent No. 12443X
(5)—Derwent No. 85028X (6) When $R^2$ is a single bond and $R^3$ is a hydrogen atom, from compounds of general formula XVI depicted hereafter, which may be prepared as described in British Patent Specification No. 1482928, by the series of reactions depicted schematically below in Scheme A, wherein $R^{14}$ represents an alkanoyl group containing from 2 to 5 carbon atoms and the other symbols are as hereinbefore defined.

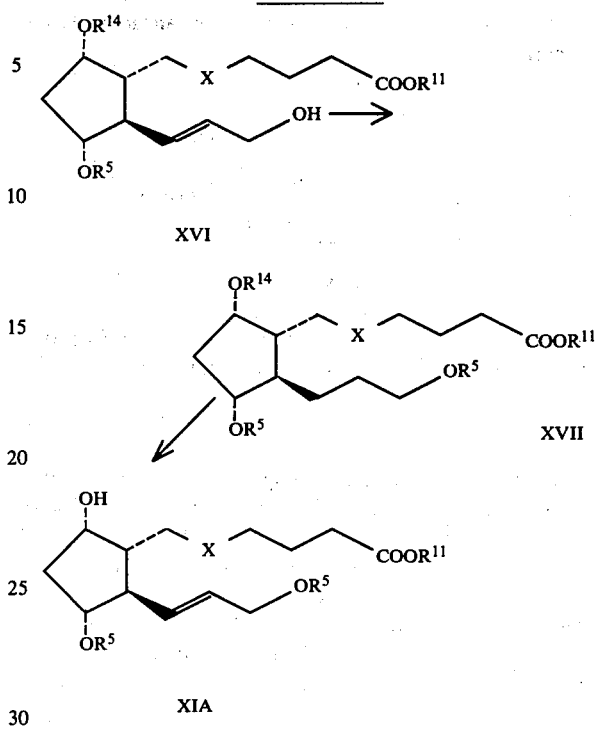

SCHEME A

Compounds of general formula XVII may be prepared by converting the hydroxy group of a compound of the general formula XVI to a protected hydroxy group by known methods. For example, methods for the conversion are described in "Protective Groups in Organic Chemistry", Chapter 3 (1973), Plenum Press, particularly ibid, pp 104–106 for the conversion of a hydroxy group to a tetrahydropyran-2-yl group which is preferable as $R^5$. For example, when $R^5$ is a heterocyclic group or an ether group, the conversion may be effected by using 2,3-dihydropyran, 2,3-dihydrofuran, 2,3-dihydrothiopyran, ethyl vinyl ether, 2-methoxypropene, 1-methoxycyclohexene or α-methoxystyrene in an inert organic solvent such as methylene chloride in the presence of a condensing agent, e.g. p-toluenesulphonic acid, sulphuric acid, trifluoroborane-etherate or phosphorus oxychloride at a temperature from ambient to 30° C., preferably at ambient temperature, or when $R^5$ is a trisubstituted silyl group, the reaction may be effected by using a tri-substituted silylating reagent, e.g. trimethylchlorosilane or trimethylsilyldiethylamine in the absence or presence of a tertiary amine such as pyridine or triethylamine in an inert organic solvent such as methylene chloride or acetone at a temperature from ambient to 30° C.

Compounds of the general formula XVII may be converted into compounds of the general formula XIA by hydrolysis under alkaline conditions, which may be effected with anhydrous potassium carbonate in an anhydrous alkanol containing at most four carbon atoms, preferably absolute methanol.

Compounds of general formula VIII or X can be obtained according to the process described in Japanese Patent Kokai Nos. 95250/75, 96543/75, 25745/77, 27753/77 and 40742/78, British Patent Specifications Nos. 1483240, 1521747, 1545213 and British Patent Application No. 35080/76, U.S. Pat. Nos. 4,024,174, 4,065,632, 4,087,620 and 4,195,182, and Belgian Pat. Nos. 823778, 845348 and 844256.

Cyclodextrin clathrates of the compounds of general formula IVA can be prepared by dissolving the cyclodextrin in water or a water-miscible organic solvent, and adding to the solution the prostaglandin analogue in a water-miscible organic solvent. The mixture is then heated and the desired cyclodextrin clathrate is isolated from the resulting solution by concentrating the mixture under reduced pressure, or by cooling and separating the product by filtration or decantation. The ratio of organic solvent to water may be varied according to the solubilities of the starting materials and products. Preferably, the temperature is not allowed to exceed 70° C. during preparation of the cyclodextrin clathrate. $\alpha$-, $\beta$- or $\gamma$-Cyclodextrin, or mixtures thereof, may be used to prepare the cyclodextrin clathrates. Conversion into cyclodextrin clathrates serves to increase the stability of the prostaglandin analogues of general formula IVA.

The prostaglandin analogues of general formula IVA and cyclodextrin clathrates thereof show, in particular, stimulatory activity on uterine contraction in a selective fashion among the various pharmacological activities which are typical of prostaglandins, and are useful in the termination of pregnancy and induction of labour in pregnant female mammals and in contraception and menstrual regulation in female mammals. In addition to the above-mentioned valuable pharmacological property the compounds of general formula IVA and cyclodextrin clathrates thereof possess relatively weak other prostaglandin-like activities such as hypotensive activity and inhibitory activity on blood platelet aggregation, and diarrhoea-producing activity. For example, in standard laboratory tests, (i) (2E,5Z,13E) (11$\alpha$,15R)-N-methanesulphonyl-9-oxo-11, 15-dihydroxy-16-(4-chlorophenoxy)-17,18,19,20-tetranorprosta-2,5,13-trien-1-amide (abbreviated to 'ONO-1' hereinafter) and (2E, 13E)-(11$\alpha$,15R)-N-methanesulphonyl-9-oxo-11,15-dihydroxy-16,16-dimethylprosta-2,13-dien-1-amide (abbreviated to 'ONO-2' hereinafter) stimulate uterine contraction in the pregnant female rat when administered intravenously on the 20th day of gestation at the doses of 0.5–1.0 and 0.5 $\mu$g/kg animal body weight, respectively, (ii) by intravenous administration to the allobarbitalanaesthetized dog, ONO-2 produces a fall in blood pressure of 14 mmHg and 44 mmHg lasting 22 and 28 minutes at the doses of 10 and 20 $\mu$g/kg animal body weight, respectively, (iii) ONO-2 produces a 50% inhibition of adenosine diphosphate-induced blood platelet aggregation in platelet-rich plasma of rats at the concentration of 26.8 $\mu$g/ml in comparison with controls, and (iv) the doses by oral administration of ONO-1 and ONO-2 required to produce diarrhoea in 50% of mice so treated are 10–20 and 10–20 mg/kg animal body weight, respectively.

Compounds of general formula IVB are new and useful intermediates for the preparation of compounds of general formula IVA.

Particularly preferred prostaglandin analogues of the present invention are as follows (abbreviating (2E, 13E)-(11$\alpha$,15$\alpha$)-N-methanesulphonyl-9-oxo-11,15-dihydroxyprosta-2,13-dien-1-amide to trans-$\Delta^2$-PGE methanesulphonyl amide):

trans-$\Delta^2$-PGE$_1$ methanesulphonyl amide,
16-methyl-trans-$\Delta^2$-PGE$_1$ methanesulphonyl amide,
17-methyl-trans-$\Delta^2$-PGE$_1$ methanesulphonyl amide,
16,16-dimethyl-trans-$\Delta^2$-PGE$_1$ methanesulphonyl amide,
20-methyl-trans-$\Delta^2$-PGE$_1$ methanesulphonyl amide,
17,20-dimethyl-trans-$\Delta^2$-PGE$_1$ methanesulphonyl amide,
15-cyclopentyl-16,17,18,19,20-pentanor-trans-$\Delta^2$-PGE$_1$ methanesulphonyl amide,
16-cyclopentyl-17,18,19,20-tetranor-trans-$\Delta^2$-PGE$_1$ methanesulphonyl amide,
17-cyclopentyl-18,19,20-trinor-trans-$\Delta^2$-PGE$_1$ methanesulphonyl amide,
15-(3-ethyl)cyclopentyl-16,17,18,19,20-pentanor-trans-$\Delta^2$-PGE$_1$ methanesulphonyl amide,
15-(3-propyl)cyclopentyl-16,17,18,19,20-pentanor-trans-$\Delta^2$-PGE$_1$ methanesulphonyl amide,
15-(3-butyl)cyclopentyl-16,17,18,19,20-pentanor-trans-$\Delta^2$-PGE$_1$ methanesulphonyl amide,
15-cyclohexyl-16,17,18,19,20-pentanor-trans-$\Delta^2$-PGE$_1$ methanesulphonyl amide,
16-cyclohexyl-17,18,19,20-tetranor-trans-$\Delta^2$-PGE$_1$ methanesulphonyl amide,
17-cyclohexyl-18,19,20-trinor-trans-$\Delta^2$-PGE$_1$ methanesulphonyl amide,
15-(4-methyl)cyclohexyl-16,17,18,19,20-pentanor-trans-$\Delta^2$-PGE$_1$ methanesulphonyl amide,
15-(4-propyl)cyclohexyl-16,17,18,19,20-pentanor-trans-$\Delta^2$-PGE$_1$ methanesulphonyl amide,
16-phenoxy-17,18,19,20-tetranor-trans-$\Delta^2$-PGE$_1$ methanesulphonyl amide,
17-phenyl-18,19,20-trinor-trans-$\Delta^2$-PGE$_1$ methanesulphonyl amide,
16-phenoxy-17,18,19,20-tetranor-trans-$\Delta^2$-PGE$_1$ methanesulphonyl amide,
16-(3-chlorophenoxy)-17,18,19,20-tetranor-trans-$\Delta^2$-PGE$_1$ methanesulphonyl amide,
16-(4-chlorophenoxy)-17,18,19,20-tetranor-trans-$\Delta^2$-PGE$_1$ methanesulphonyl amide,
16-(3-trifluoromethylphenoxy)-17,18,19,20-tetranor-trans-$\Delta^2$-PGE$_1$ methanesulphonyl amide,
and the corresponding PGE$_2$ analogues, and cyclodextrin clathrates thereof.

The most preferred prostaglandin analogues of the invention are 16-(4-chlorophenoxy)-17,18,19,20-tetranor-trans-$\Delta^2$-PGE$_2$ methanesulphonyl amide, i.e. (2E,5Z,13E)-(11$\alpha$,15R)-N-methanesulphonyl-9-oxo-11,15-dihydroxy-16-(4-chlorophenoxy)-17,18,19,20-tetranorprosta-2,5,13-trien-1-amide and 16,16-dimethyl-trans-$\Delta^2$-PGE$_1$ methanesulphonyl amide, i.e. (2E,13E)-(11$\alpha$,15R)-N-methanesulphonyl-9-oxo-11,15-dihydroxy-16,16-dimethylprosta-2,13-dien-1-amide.

The following Reference Examples and Examples illustrate the preparation of compounds of the present invention. In the Reference Examples and Examples "TLC", "IR", "NMR", and "MS" represent, respectively, "thin layer chromatography", "infrared absorption spectrum", "nuclear magnetic resonance spectrum", and "mass spectrometry". Where solvent ratios are specified in chromatographic separations the ratios are by volume: solvents shown in parenthesis are used as developing solvents. Unless otherwise specified, infrared absorption spectra were measured by the liquid film method, and nuclear magnetic resonance spectra were measured in deuterochloroform (CDCl$_3$) solution.

REFERENCE EXAMPLE 1

(5Z,13E)-(9α,11α,15R)-9-Hydroxy-11,15-bis(tetrahydropyran-2-yloxy)-16-(4-chlorophenoxy)-17,18,19,20-tetranorprosta-5,13-dienoic acid methyl ester A mixture of 1.76 g of (5Z, 13E)-(9α,11α,15R)-9-acetoxy-11-(tetrahydropyran-2-yloxy)-15-hydroxy-16-(4-chlorophenoxy)-17,18,19,20-tetranorprosta-5,13-dienoic acid methyl ester (the compound described in Reference Example 21 in British Patent Specification No. 1,521,747), 6 mg of p-toluenesulphonic acid, 0.27 ml of 2,3-dihydropyran, and 10 ml of methylene chloride was stirred at room temperature for 10 minutes. The pH of the reaction solution obtained was adjusted to 8 with a saturated aqueous solution of sodium bicarbonate, and the solution was then extracted with ethyl acetate. The extract was washed with a saturated aqueous solution of sodium chloride, dried over anhydrous magnesium sulphate and concentrated under reduced pressure to obtain (5Z, 13E)-(9α,11α,15R)-9-acetoxy-11,15-bis(tetrahydropyran-2-yloxy)-16-(4-chlorophenoxy)-17,18,19,20-tetranorprosta-5,13-dienoic acid methyl ester having the following physical characteristic:

TLC (cyclohexane:ethyl acetate=1:1): Rf=0.54.

The product thus obtained and 516 mg of potassium carbonate dissolved in 20 ml of methanol were stirred for one hour at 50° to 55° C. The pH of the reaction solution was adjusted to 4 with acetic acid, and the solution was then concentrated under reduced pressure. The resulting residue was dissolved in ethyl acetate, washed successively with water, a saturated aqueous solution of sodium bicarbonate, and a saturated aqueous solution of sodium chloride, dried over anhydrous magnesium sulphate, and concentrated under reduced pressure. The residue was purified by column chromatography on silica gel using a mixture of cyclohexane-ethyl acetate (3:1) as eluent to obtain 1.58 g of the title compound having the following physical characteristics:

TLC (cyclohexane:ethyl acetate=1:1): Rf=0.40;
IR: $\nu=1740$ cm$^{-1}$;
NMR: $\delta=7.13$ (2H, d), 6.73 (2H, d), 5.75–5.20 (4H, m), 3.58 (3H, s).

REFERENCE EXAMPLE 2

(13E)-(2RS,9α,11α,15R)-2-Phenylseleno-9-hydroxy-11,15-bis(tetrahydropyran-2-yloxy)-16,16-dimethylprost-13-enoic acid methyl ester Under an atmosphere of nitrogen, 28 ml of a 1.5 M solution of butyllithium in hexane were added dropwise to 6.65 ml of diisopropylamine in 250 ml of tetrahydrofuran at −70° C., and the mixture was stirred for 30 minutes at the same temperature. 9.59 g of (13E)-(9α,11α,15R)-9-hydroxy-11,15-bis(tetrahydropyran-2-yloxy)-16,16-dimethylprost-13-enoic acid methyl ester (the compound described in Reference Example 13 of British Patent Specification No. 1,540,427) in 50 ml of tetrahydrofuran were added dropwise thereto at −70° C., and the mixture was stirred for 30 minutes at the same temperature. 14.7 g of diphenyl diselenide in 50 ml of tetrahydrofuran was added to the reaction solution obtained, and the mixture was stirred for 10 minutes at −70° C. The reaction solution was then poured into 300 ml of a saturated aqueous solution of ammonium chloride, and the mixture was extracted with ethyl acetate. The extract was washed successively with water and a saturated aqueous solution of sodium chloride, dried over anhydrous magnesium sulphate, and concentrated under reduced pressure. The residue was purified by column chromatography on silica gel using a mixture of methylene chloride-ethyl acetate (2:1) as eluent to obtain 11.46 g of the title compound having the following physical characteristics:

TLC (benzene:ethyl acetate=2:1): Rf=0.50;
IR: $\nu=3500$, 2950, 2860, 1740, 1600, 1250, 1030, 980 cm$^{-1}$;
NMR: $\delta=7.7$–7.0 (5H, m), 5.6–5.0 (2H, m), 4.8–4.3 (2H, m) 4.3–3.0 (8H, m), 3.6 (3H, s).

The following compound was obtained in the same manner from the product of Reference Example 1.

(a) (5Z, 13E)-(2RS,9α,11α,15R)-2-Phenylseleno-9-hydroxy-11,15-bis(tetrahydropyran-2-yloxy)-16-(4-chlorophenoxy)-17,18,19,20-tetranorprosta-5,13-dienoic acid methyl ester:

TLC (benzene:ethyl acetate=2:1): Rf=0.61;
IR: $\nu=3500$, 2950, 2860, 1740, 1590, 1490, 1140, 1030, 980 cm$^{-1}$;
NMR: $\delta=7.7$–7.0 (5H, m), 7.15–6.7 (4H, m), 5.9–5.1 (4H, m), 5.0–4.3 (3H, m), 4.3–3.2 (9H, m), 3.62 (3H, s).

REFERENCE EXAMPLE 3

(5Z, 13E)-(2RS,9α,11α,15R)-2-Phenylseleno-9-hydroxy-11,15-bis(tetrahydropyran-2-yloxy)-16-(4-chlorophenoxy)-17,18,19,20-tetranorprosta-5,13-dienoic acid A mixture of 1.06 g of the ester [prepared as described in Reference Example 2(a)], 40 ml of ethanol, and 20 ml of a 2 N aqueous potassium hydroxide solution was stirred for one hour at 40° C. 100 ml of diethyl ether were added to the reaction solution obtained, and the solution was then neutralised with 1 N hydrochloric acid at 0° C. and extracted with ethyl acetate. The extract was washed successively with water and a saturated aqueous solution of sodium chloride, dried over anhydrous magnesium sulphate, and concentrated under reduced pressure. The residue was purified by column chromatography on silica gel using a mixture of ethyl acetate-cyclohexane (5:4) as eluent to obtain 600 mg of the title compound having the following physical characteristics:

TLC (ethyl acetate:benzene=2:1): Rf=0.37;
IR: $\nu=3350$, 1740, 1601, 1585, 1495, 1250, 980 cm$^{-1}$;
NMR: $\delta=7.9$–6.1 (9H, m), 6.0–5.1 (6H, m), 4.95–4.3 (3H, m).

The following compound was obtained in the same manner from the product of Reference Example 2.

(a) (13E)-(2RS,9α,11α,15R)-2-Phenylseleno-9-hydroxy-11,15-bis(tetrahydropyran-2-yloxy)-16,16-dimethylprost-13-enoic acid:

TLC (methylene chloride:methanol=19:1): Rf=0.16;
NMR: $\delta=7.7$–7.0 (5H, m), 6.0–5.1 (4H, m), 4.8–4.3 (2H, m), 4.3–3.0 (8H, m).

REFERENCE EXAMPLE 4

(5Z, 13E)-(2RS,9α,11α,15R)-N-Methanesulphonyl-2-phenylseleno-9-hydroxy-11,15-bis(tetrahydropyran-2-yloxy)-16-(4-chlorophenoxy)-17,18,19,20-tetranorprosta-5,13-dien-1-amide Under an atmosphere of nitrogen, 0.1 ml of triethylamine and 0.092 ml of isobutyl chloroformate were added to 410 mg of the dienoic acid (prepared as described in Reference Example 3) in 3 ml of N,N-dimethylformamide, and the mixture was stirred at 0° C. for 30 minutes. 340 mg of sodium methanesulphonamide and 0.62 ml of hexamethylphosphoramide were added to the reaction mixture, and the mixture was stirred at room temperature for 16 hours. The pH of the reaction solution was adjusted to 5 using 1 N hydrochloric acid at 0° C., and the solution was then diluted with 10 ml of water and extracted with ethyl acetate. The extract was washed successively with water and a saturated aqueous solution of sodium chloride, dried over anhydrous magnesium sulphate, and concentrated under reduced pressure. The residue was purified by column chromatography on silica gel using ethyl acetate as eluent to obtain 295 mg of the title compound having the following physical characteristics:

TLC (ethyl acetate:benzene=2:1): Rf=0.53;

IR: $\nu$=1720, 1625, 1605, 1590, 1495, 1350, 1250, 1120, 985 cm$^{-1}$;

NMR: $\delta$=7.8–6.5 (9H, m), 5.9–5.1 (4H, m), 5.0–4.3 (3H, m), 3.05 and 3.00 (3H, each s).

The following compound was obtained in the same manner from the acid of Reference Example 3(a).

(a) (13E)-(2RS,9α,11α,15R)-N-Methanesulphonyl-2-phenylseleno-9-hydroxy-11,15-bis(tetrahydropyran-2-yloxy)-16,16-dimethylprost-13-en-amide:

TLC (ethyl acetate:benzene=3:1): Rf=0.56;

IR (chloroform solution): $\nu$=2930, 2860, 1720, 1600, 1400, 1340, 1160, 1120, 1020, 980 cm$^{-1}$;

NMR: $\delta$=9.4–8.6 (1H, m), 7.7–7.0 (5H, m), 5.6–5.0 (2H, m), 4.8–4.3 (2H, m), 4.3–3.0 (8H, m), 3.05 (3H, s).

REFERENCE EXAMPLE 5

(2E,5Z,13E)-(9α,11α,15R)-N-Methanesulphonyl-9-hydroxy-11,15-bis(tetrahydropyran-2-yloxy)-16-(4-chlorophenoxy)-17,18,19,20-tetranorprosta-2,5,13-trien-1-amide 0.22 ml of 30% v/v hydrogen peroxide was added dropwise to a mixture of 295 mg of the phenylseleno compound (prepared as described in Reference Example 4), 147 mg of calcium carbonate, 10 ml of ethyl acetate, and 5 ml of tetrahydrofuran at 40° C., and the resulting mixture was stirred for 30 minutes at the same temperature. The reaction mixture was then diluted with 30 ml of water and extracted with ethyl acetate. The extract was washed successively with a saturated aqueous solution of sodium bicarbonate and a saturated aqueous solution of sodium chloride, dried over anhydrous magnesium sulphate, and concentrated under reduced pressure. The residue was purified by column chromatography on silica gel using a mixture of ethyl acetate and benzene (1:1) as eluent to obtain 210 mg of the title compound having the following physical characteristics:

TLC (ethyl acetate:benzene=2:1): Rf=0.45;

IR: $\nu$=1700, 1640, 1595, 1490, 1345, 1125, 975 cm$^{-1}$;

NMR: $\delta$=7.3–6.7 (5H, m), 5.92 (1H, d), 5.9–5.2 (4H, m), 5.0–4.4 (3H, m), 3.28 (3H, s), 3.15–2.8 (2H, m).

The following compound was obtained in the same manner from the phenylseleno compound of Reference Example 4(a).

(a) (2E, 13E)-(9α,11α,15R)-N-Methanesulphonyl-9-hydroxy-11,15-bis(tetrahydropyran-2-yloxy)-16,16-dimethylprosta-2,13-dien-1-amide:

TLC (ethyl acetate:benzene=3:1): Rf=0.45;

NMR: $\delta$=9.2–8.8 (1H, m), 6.9 (1H, dd), 5.8 (1H, d), 5.6–5.2 (2H, m), 4.8–4.5 (2H, m), 4.3–3.1 (7H, m), 3.23 (3H, s), 1.0–0.6 (9H, m).

EXAMPLE 1

(2E,5Z,13E)-(11α,15R)-N-Methanesulphonyl-9-oxo-11,15-bis(tetrahydropyran-2-yloxy)-16-(4-chlorophenoxy)-17,18,19,20-tetranorprosta-2,5,13-trien-1-amide A mixture of 210 mg of the hydroxy compound (prepared as described in Reference Example 5), 5.4 ml of diethyl ether, and an ice-cooled chromic acid solution (prepared from 303 mg of chromium trioxide, 2.31 g of manganese sulphate, 0.265 ml of concentrated sulphuric acid, and 4.8 ml of water) was stirred for one hour with ice-cooling. The reaction mixture was extracted with diethyl ether. The extract was washed successively with water and a saturated aqueous solution of sodium chloride, dried over anhydrous magnesium sulphate, and concentrated under reduced pressure. The residue was purified by column chromatography on silica gel using a mixture of methylene chloride and ethanol (100:3) as eluent to obtain 180 mg of the title compound having the following physical characteristics:

TLC (ethyl acetate:benzene=2:1): Rf=0.51;

IR: $\nu$=1740, 1710, 1640, 1600, 1490, 1350, 1245, 1130, 980 cm$^{-1}$;

NMR: $\delta$=7.4–6.3 (5H, m), 5.91 (1H, d), 5.9–5.1 (4H, m), 5.0–4.3 (3H, m), 3.3 (3H, s), 3.1–2.8 (2H, m).

The following compound was obtained in the same manner from the hydroxy compound of Reference Example 5(a).

(a) (2E, 13E)-(11α,15R)-N-Methanesulphonyl-9-oxo-11,15-bis-(tetrahydropyran-2-yloxy)-16,16-dimethylprosta-2,13-dien-1-amide;

TLC (ethyl acetate:benzene=3:1): Rf=0.77;

NMR: $\delta$=9.2–8.8 (1H, m), 6.9 (1H, dd), 5.8 (1H, d), 5.8–5.4 (2H, m), 4.8–4.5 (2H, m), 4.4–3.1 (6H, m), 3.3 (3H, s), 1.0–0.6 (9H, m).

EXAMPLE 2

(2E,5Z,13E)-(11α,15R)-N-Methanesulphonyl-9-oxo-11,15-dihydroxy-16-(4-chlorophenoxy)-17,18,19,20-tetranorprosta-2,5,13-trien-1-amide A mixture of 180 mg of the tetrahydropyran-2-yloxy compound (prepared as described in Example 1), 0.2 ml of tetrahydrofuran, and 2 ml of 65% v/v aqueous acetic acid was stirred for 2 hours at 40° C. The reaction solution obtained was poured into 10 ml of ice-water and the mixture was extracted with ethyl acetate. The extract was then washed successively with water and a saturated aqueous solution of sodium chloride, dried over anhydrous magnesium sulphate, and concentrated under reduced pressure. The residue was purified by column chromatography on silica gel using a mixture of ethyl acetate and cyclohexane (10:1) as eluent to obtain 52 mg of the title compound having the following physical characteristics:

TLC (chloroform:tetrahydrofuran:acetate acid=10:2:1): Rf=0.22;

IR: $\nu$=1744, 1703, 1640, 1600, 1585, 1495, 1450, 1340, 1250, 1125, 975 cm$^{-1}$;

NMR: $\delta$7.4–6.6 (5H, m), 5.95 (1H, d), 5.93–5.2 (4H, m), 4.7–4.4 (1H, m), 4.4–3.8 (3H, m), 3.27 (3H, s), 3.1–2.8 (2H, m).

The following compound was obtained in the same manner from the compound of Example 1(a).

(a) (2E, 13E)-(11α,15R)-N-Methanesulphonyl-9-oxo-11,15-dihydroxy-16,16-dimethylprosta-2,13-dien-1-amide;

Melting point: 54°-55° C. (recrystallised from ethyl acetate and hexane);

TLC (benzene:dioxan:acetic acid=20:10:1): Rf=0.30;

IR (KBr disc): $\nu$=2930, 2860, 1735, 1700, 1640, 1450, 1340, 1120, 970 cm$^{-1}$;

NMR: $\nu$=9.4–9.2 (1H, m), 7.04 (1H, dt), 5.8 (1H, d), 5.8–5.5 (2H, m), 4.2–3.7 (2H, m), 3.33 (3H, s), 2.75 (1H, dd), 1.0–0.6 (9H, m).

The present invention includes within its scope pharmaceutical compositions which comprise at least one compound of general formula IVA or cyclodextrin clathrate thereof, together with a pharmaceutical carrier or coating. In clinical practice, the compounds of general formula IVA and their cyclodextrin clathrates will normally be administered orally, intravaginally, intrarectally or parenterally.

Solid compositions for oral administration include compressed tablets, pills, dispersible powders, and granules. In such solid compositions, one or more of the active ingredients is or are admixed with at least one inert diluent such as calcium carbonate, potato starch, dextrin, alginic acid, lactose, mannitol, glucose or cacao butter. The compositions may also comprise, as is normal practice, additional substances other than inert diluents, e.g. lubricating agents, such as magnesium stearate. If desired, tablets or pills may be coated with sugar or gelatin, an enteric substance or film, or with two or more such layers.

Liquid compositions for oral administration include pharmaceutically acceptable emulsions, solutions, suspensions, syrups and elixirs, containing inert diluents commonly used in the art, such as water or liquid paraffin. Besides inert diluents such compositions may also comprise adjuvants, e.g. wetting agents and suspending agents, and sweetening, flavouring, perfuming and preserving agents.

Compositions according to the present invention for oral administration also include capsules of an absorbable material such as gelatin containing one or more of the active compounds with or without the addition of diluents or excipients.

Solid compositions for intrarectal administration include suppositories formulated in manner known per se and containing one or more of the active compounds.

Solid or ointment compositions for intravaginal administration include pessaries, e.g. silicone rubber pessaries, and ointments which comprise one or more carriers, diluents or supports (e.g. cacao butter, macrogol, Witepsol, silicone rubber or Vaseline) containing one or more of the active ingredients and which are formulated according to methods known per se. "Witepsol" and "Vaseline" are registered Trade Marks. Particularly preferred compositions for intravaginal administration are film compositions, formulated in manner known per se, which comprise one or more of the active compounds, and as support, one or more water-soluble polymers (for example, hydroxypropyl cellulose, polyvinyl pyrrolidone, hydroxypropylmethyl cellulose, and polyacrylic acid) and/or water-insoluble polymers (for example, cellulose acetate, and polyvinyl acetate), one or more plasticisers, for example, diethyl phthalate, dibutyl phthalate, butyl phthalylbutyl glycolate, diethylene glycol, triethylene glycol, dipropylene glycol, polyethylene glycol, glycerol, diacetin, triacetin, tributyrin or Myvacet and, if desired, one or more organic acids or anhydrides (for example citric acid, citric anhydride, tartaric acid, tartaric anhydride, succinic acid, stearic acid, or palmitic acid). "Myvacet" is a registered Trade Mark.

Preparations according to the present invention for parenteral administration include sterile aqueous or non-aqueous solutions, suspensions and emulsions. Examples of non-aqueous solvents or suspending media are propylene glycol, polyethylene glycol, ethanol, vegetable oils (e.g. olive oil), and injectable organic acid esters (e.g. ethyl oleate and sorbitan esters). These compositions may also include adjuvants such as preserving, wetting, emulsifying and dispersing agents. They may be sterilised, for example, by filtration through a bacteria-retaining filter, by incorporation of sterilising agents in the compositions, or by irradiation. They may also be manufactured in the form of sterile solid compositions, which can be dissolved in sterile water or some other sterile injectable medium immediately before use.

The percentage of active ingredient in the compositions of the present invention may be varied, it being necessary that it should constitute a proportion such that a suitable dosage for the desired therapeutic effect shall be obtained. Several unit dosage forms may of course be administered at the same time. In general the preparations should normally contain at least 0.025% by weight of active substance when required for administration by injection; for oral administration the preparations will normally contain at least 0.1 wt % of active substance.

The dosage employed depends upon, for example, the desired therapeutic effect, the route of administration, the duration of the treatment, age and body weight.

In the human adult, the doses per person are generally between 5 $\mu$g and 5 mg by oral, intravaginal, intrauterine, intrarectal, intravenous, intramuscular or extraovular administration for contraception and menstrual regulation in women or in the termination of pregnancy and induction of labour in pregnant women. In domestic female mammals such as cows, mares, sows, ewes and bitches, the doses are generally between 0.001 and 50 mg per animal by intramuscular, subcutaneous, intrauterine, intravaginal or intravenous administration in the induction of abortion and labour.

The following Examples illustrate pharmaceutical compositions of the present invention.

EXAMPLE 3

1000 Tablets containing 0.5 mg of active ingredient per tablet were obtained in a conventional manner from 500 mg of (2E, 13E)-(11$\alpha$,15R)-N-methanesulphonyl-9-oxo-11,15-dihydroxy-16,16-dimethylprosta-2,13-dien-1-amide, 2 g of carboxymethyl cellulose calcium salt, 0.2 g of silicon dioxide, 2 g of magnesium stearate, and 95.3 g of mannitol.

EXAMPLE 4

100 Pessaries containing 1 mg of active ingredient per pessary were obtained in a conventional manner from 100 mg of (2E, 13E)-(11$\alpha$,15R)-N-methanesulphonyl-9-oxo-11,15-dihydroxy-16,16-dimethylprosta-2,13-dien-1-amide, 2 ml of ethanol, and 80 g of Witepsol S-52.

EXAMPLE 5

50 Silicone rubber pessaries containing 1 mg of active ingredient per silicone rubber pessary were obtained in a conventional manner from 50 mg of (2E, 13E)-(11$\alpha$-15R)-N-methanesulphonyl-9-oxo-11,15-dihydroxy-16,16-dimethylprosta-2,13-dien-1-amide, 10 ml of ethanol, 100 sheets of silicone rubber (0.25 mm in thickness and 10 cm² in area), and gelatin (as an adhesive).

EXAMPLE 6

A film composition was prepared in a conventional manner from 0.2 mg of (2E, 13E)-(11α,15R)-N-methanesulphonyl-9-oxo-11,15-dihydroxy-16,16-dimethylprosta-2,13-dien-1-amide, 199.5 mg of hydroxypropyl cellulose, 0.3 mg of citric anhydride, and 3 ml of methanol.

EXAMPLE 7

A film composition was prepared in a conventional manner from 0.2 mg of (2E, 13E)-(11α,15R)-N-methanesulphonyl-9-oxo-11,15-dihydroxy-16,16-dimethylprosta-2,13-dien-1-amide, 20 mg of polyvinyl acetate, 10 mg of glycerol, 10 mg of triacetin, 160 mg of hydroxypropyl cellulose, 0.3 mg of tartaric anhydride, and 3 ml of methanol.

We claim:

1. A prostaglandin analogue of the formula:

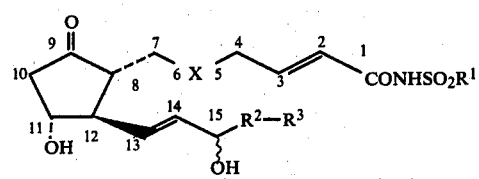

IV (wherein $R^1$ represents an alkyl group containing from 1 to 4 carbon atoms, $R^2$ represents a single bond or an alkylene group containing from 1 to 5 carbon atoms, $R^3$ represents an alkyl group containing from 1 to 8 carbon atoms, X represents an ethylene group or a cis-vinylene group, the double bonds between the carbon atoms in positions 2 and 3 and between the carbon atoms in positions 13 and 14 are both in trans-configuration, and the wavy line ∼∼ attached to the carbon atom in position 15 represents α- or β-configuration or a mixture thereof), or a cyclodextrin clathrate thereof.

2. A prostaglandin analogue according to claim 1, wherein $R^1$ represents a methyl group.

3. A prostaglandin analogue according to claim 1, wherein the grouping —$R^2$—$R^3$ represents n-pentyl or n-hexyl unsubstituted or substituted by one or two methyl group(s).

4. A prostaglandin analogue according to claim 1, wherein the grouping —$R^2$—$R^3$ represents n-pentyl, 1-methylpentyl, 2-methylpentyl, 1,1-dimethylpentyl, hexyl or 2-methylhexyl.

5. A prostaglandin analogue according to claim 1, wherein the grouping —$R^2$—$R^3$ represents 1,1-dimethylpentyl.

6. A prostaglandin analogue according to claim 1, wherein the group OH atached to the C-15 carbon atom in formula IV depicted in claim 1 is in α-configuration.

7. A compound according to claim 1 which is (2E, 13E)-(11α,15R)-N-methanesulphonyl-9-oxo-11,15-dihydroxy-16,16-dimethylprosta-2,13-dien-1amide or a cyclodextrin clathrate thereof.

8. A compound according to claim 1 which is a cyclodextrin clathrate of a prostaglandin analogue claimed in any one of claims 1 to 6.

9. A pharmaceutical composition useful in the termination of pregnancy or induction of labour in pregnant female mammals and in contraception and menstrual regulation in female mammals which comprises an effective amount of at least one prostaglandin analogue of general formula IV claimed in claim 1 or cyclodextrin clathrate thereof, in association with a pharmaceutical carrier or coating.

10. A pharmaceutical composition according to claim 9 in which the active ingredient is (2E, 13E)-(11α,15R)-N-methanesulphonyl-9-oxo-11,15-dihydroxy-16,16-dimethylprosta-2,13-dien-1-amide or a cyclodextrin clathrate thereof.

11. A method for the termination of pregnancy or induction of labour in a pregnant female mammal or for contraception or menstrual regulation in a female mammal which comprises administering an effective amount of a compound of general formula IV specified in claim 1, or a cyclodextrin clathrate thereof.

* * * * *